United States Patent [19]

Kano et al.

[11] 4,303,616
[45] Dec. 1, 1981

[54] AGGLUTINATION ANALYZING VESSEL

[75] Inventors: Tokio Kano, Akishima; Akira Tamagawa, Fuchu, both of Japan

[73] Assignee: Olympus Optical Co. Ltd., Tokyo, Japan

[21] Appl. No.: 159,000

[22] Filed: Jun. 12, 1980

[30] Foreign Application Priority Data

Jun. 20, 1979 [JP] Japan .................................. 54-77643

[51] Int. Cl.³ ........................ B01L 3/00; G01N 33/54
[52] U.S. Cl. ................................ 422/102; 23/915; 356/246; 422/73
[58] Field of Search ................. 422/73, 102; 23/230 B, 23/915; 215/DIG. 3; 356/246

[56] References Cited

U.S. PATENT DOCUMENTS 3,190,731  6/1965  Weiskopf ........................... 422/102
3,876,380  4/1975  Helriegel ........................... 422/102

FOREIGN PATENT DOCUMENTS 2915145  10/1979  Fed. Rep. of Germany ........ 23/915

*Primary Examiner*—Arnold Turk
*Attorney, Agent, or Firm*—Haseltine and Lake

[57] ABSTRACT

An agglutination analyzing vessel which is provided on at least one portion of a base surface thereof with an inclined surface which is provided on at least one portion thereof with a plurality of engravings regularly arranged and forming a stable state of settling down particles on the inclined base surface.

11 Claims, 8 Drawing Figures

AGGLUTINATION ANALYZING VESSEL

BACKGROUND OF THE INVENTION

1. Field of the Invention

This invention relates to an agglutination analyzing vessel for analyzing agglutination patterns produced in response to immunological agglutination reactions and more particularly to a vessel for identifying various kinds of blood types with the aid of agglutination patterns of blood corpuscles or for detecting various kinds of antibodies and various antigens in sample solutions (like viruses, proteins or the like) with the aid of agglutination patterns of not only blood corpuscles but also of particles of materials such as latex, carbon or the like.

2. Description of the Prior Art

In a conventional method of identifying blood types, for example, which has heretofore been proposed, use was made of a winecup-shaped reaction vessel into which was quantitatively introduced a sample solution, 2 to 5% of test blood corpuscles suspended in saline solution, and a specified antiserum. Then, the mixture was set stationary for reaction between blood corpuscles and antiserum. Subsequently, it was centrifuged to sediment blood corpuscles. Then, the reaction vessel was rapidly wobbled such that the sedimented blood corpuscles were forcedly separated one from the other and then relatively slowly wobbled so as to collect the clumped compositions in the center portion of the base surface of the vessel and form settling patterns, and then photometrically detecting these patterns.

Such conventional blood type identifying method in which sedimentation is effected and then the reaction vessel is rapidly wobbled so as to separate the sedimented blood corpuscles from the base surface of the vessel can only be applied to the analysis of regular ABO blood type which shows strong agglutination, but could not be applied to many other immunological agglutination reactions which show weak agglutination, for example, a method of determining Rh blood subtype or detecting various kinds of incomplete antibodies. That is, if the agglutination reaction is weak, the blood corpuscles or the like which have been clumped together become separated one from other when the reaction vessel is wobbled, and as a result, the particles are not collected in the center portion of the reaction vessel.

In order to detect and measure the HBs antigen, a method has been proposed which makes use of a plastic plate, called microplate, provided with a number of wells each having a conical base surface. This conventional method makes use of a microplate having 10×12 wells, for example, and detects and prescribes the HBs antigen by the following procedure.

(1) Diluent specially prescribed for R-PHA method is introduced into each well of the microplate one drop (0.025 ml) at a time.

(2) A test serum (0.025 ml) is added to the first well of a row. By using a diluter, the doubling dilution is performed along the row up to the last (tenth) well.

(3) One drop of R-PHA cell (0.025 ml of 1% cell suspension) is added to each well.

(4) The mixture thus treated is sufficiently agitated by the micromixer for 10 seconds so as to cause the R-PHA cell to uniformly suspend.

(5) The mixture thus treated is left stationary at room temperature for one hour and thereafter the settling patterns are detected.

In such detection method, the reaction vessel is made sufficiently stationary before the detection so that the sedimented agglutinates are not separated one from the other. However, if this method is applied to an immunological agglutination reaction of one portion which is less stable than HBs antigen particularly to the agglutination reaction due to incomplete antibodies, it is impossible to obtain a sufficiently stable, clear and precise agglutination pattern. This is because of the fact that the agglutinated particles slip down along the conical base surface of the reaction vessel in the same manner as the particles which are not agglutinated and tend to be collected in the center portion of the vessel. In order to eliminate such drawback, use has been made of a reaction vessel provided at its conical base surface with ground glass like minute indentations. Such reaction vessel, however, is irregular in arrangement, size and configuration of the indentation, and as a result, too large an amount of agglutinates are collected in one portion of the inclined surface, thereby rendering formation of the uniform agglutination patterns difficult. Thus, it is not always possible to eliminate the above mentioned drawback.

SUMMARY OF THE INVENTION

An object of the invention, therefore, is to provide an agglutination analyzing vessel which can eliminate the above mentioned drawbacks which have been encountered with the prior art techniques and which can form stable, clear, and precise agglutination patterns of particles, for example, test blood corpuscles by an immunological agglutination reaction irrespective of the strength of agglutination.

Another object of the invention is to provide an agglutination analyzing vessel which can form stable, clear, and precise agglutination patterns even when the settling down particles are red blood corpuscles having a weak agglutinating property.

A feature of the invention is the provision in an agglutination analyzing vessel which can make a test liquid containing particles in a stationary state and cause the particles to settle down so as to form agglutination patterns on the base surface of the vessel and which can effect an immunological analysis, of the improvement in which said base surface is provided on at least one portion thereof with an inclined surface which is provided on at least one portion thereof with a plurality of engravings regularly arranged and forming a stable substrate for said settling down particles on said inclined base surface.

Further features and objects of the invention will be fully understood from the following detailed description with reference to the accompanying drawings, wherein:

DETAILED DESCRIPTION OF THE PREFERRED EMBODIMENTS

Figure 1:
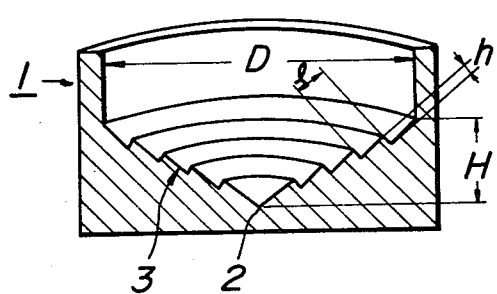
FIG. 1 is a perspective view of one embodiment of an agglutination analyzing vessel according to the invention, partly shown in section.

In the above mentioned agglutination analyzing vessel according to the invention, the engravings function to uniformly deposit and hold the settling down particles on the inclined base surface irrespective of the strength of the bonding force of the particles. In the following, the term engravings shall be understood to include uniformly spaced grooves, uniformly spaced protrusions forming grooves, and uniformly spaced depressions. The inventors have ascertained that in order to uniformly deposit and hold the settling down particles on the inclined base surface of the vessel in the case when agglutination reactions take place, it is necessary to form a stable substrate at the lowest layer of the deposited particles.

That is, if such stable substrate is formed, the particles agglutinated due to antigen-antibody reaction are deposited and held on the inclined base surface of the vessel in a stable manner, thereby forming clear and precise agglutination patterns. In accordance with the invention, regular engravings are formed for the purpose of forming the above mentioned stable substrate. This stable substrate is formed even when the settling down particles are not agglutinated. When the settling down particles are not agglutinated, they slip down along the substrate and are collected at the lowest portion of the inclined base surface. As a result, it is always possible to form stable patterns irrespective of agglutination and non-agglutination of the settling down particles and precisely analyze various agglutinations.

The dimension of the engraving formed on the inclined base surface of the reaction vessel is dependent on the size of the settling down particles. That is, if the engravings are too large as compared with the size of the settling down particles, the particles which are not agglutinated are collected in the engravings and hence are prevented from slipping down toward the lowest point of the inclined base surface of the vessel. On the contrary, if the engravings are too small as compared with the size of the settling down particles and particularly when the agglutinating force of the particles is weak, the particles slip along the engravings and are collected in the lowest point of the inclined base surface. As a result, it is impossible to form a stable substrate and hence to discriminate the agglutination patterns one from the other.

As described above, in the present invention, in order to eliminate such disadvantage, the inclined base surface of the vessel is provided on at least one portion thereof with a plurality of engravings arranged in a regular manner. It is preferable that the plurality of engravings be composed of a plurality of depressed portions each having a maximum depth of 2 to 50 $\mu$m and a length in the inclined direction of 5 to 200 $\mu$m.

Such depressed portions may be replaced by protruded portions each having a height of 2 to 50 $\mu$m and spaced apart from each other in the inclined direction by a distance of 5 to 200 $\mu$m.

If the maximum depth of the depressed portion and the height of the protruded portion are smaller than 2 $\mu$m, the settling down particles can not be held by the depressed and protruded portions. As a result, it is difficult to form a stable substrate. Particularly, if the particles have a weak agglutinating force, the particles tend to be collected in the lowest point of the inclined base surface of the vessel irrespective of the agglutination or non-agglutination of the particles. As a result, it is difficult to discriminate the pattern produced when the particles are agglutinated from the pattern produced when the particles are not agglutinated.

If the maximum depth of the depressed portion and the height of the protruded portion exceed 50 $\mu$m, the settling down particles which are not agglutinated with each other are held by such depressed or protruded portions, and as a result, clear and precise patterns are not formed.

In addition, if the length of the depressed portion and the distance between adjacent protruded portions in the inclined direction are smaller than 5 $\mu$m, it is difficult to hold the settling down particles in a stable manner. Particularly, if the particles have a weak agglutinating force, the settling down particles tend to be collected in the lowest portion of the inclined base surface of the vessel irrespective of the agglutination or non-agglutination of the particles. As a result, it is difficult to discriminate the pattern produced when the particles are agglutinated from the pattern produced when the particles are not agglutinated.

If the length of the depressed portion and the distance between adjacent protruded portions in the inclined direction exceed 200 $\mu$m, the length of the substrate in the inclined direction becomes long and hence the settling down particles tend to slip down along the inclined base surface of the vessel. As a result, it is impossible to form stable substrates and discriminate the pattern produced when the particles are agglutinated from the pattern produced when the particles are not agglutinated.

The invention will now be described with reference to the drawings. FIG. 1 shows one embodiment of an agglutination analyzing vessel according to the invention. In this embodiment, an agglutination analyzing vessel 1 is provided at its inclined base surface with a plurality of depressed portions 3 leading from the lowest point 2 of an inverted conical base surface of the vessel along the inclined base surface to the top periphery thereof located at substantially the middle point of the inner wall of the vessel and concentrically arranged about the lowest point 2 as its center in a continuous and regular manner, these depressed portions 3 being sawtoothed in section taken along a radial direction of the vessel. The vessel 1 has an inner diameter D of 6 mm. The inverted conically inclined base surface has a height H of about 1.5 mm and is inclined at about 27° with respect to the horizontal base surface of the vessel. Each depressed portion 3 has a maximum depth h of 2 to 50 $\mu$m and a length l in the inclined direction of 5 to 200 $\mu$m. The vessel 1 is formed of plastic material having a chemically resistant property and made integral into one body.

The vessel 1 constructed as above described makes it possible to maintain the sedimented particles such as blood corpuscles or the like on the depressed portions 3 and form a stable substrate on the inclined base surface of the vessel 1. As a result, the particles agglutinated with each other are effectively deposited on the stable substrate. The sedimented particles which are not agglutinated slip down along the substrate and are collected in the lowest point 2 of the inclined base surface, thereby always forming stable patterns. As a result, it is possible to discriminate a difference between various agglutinations of the sedimented particles, thereby precisely effecting the immunological analysis.

Figure 2:
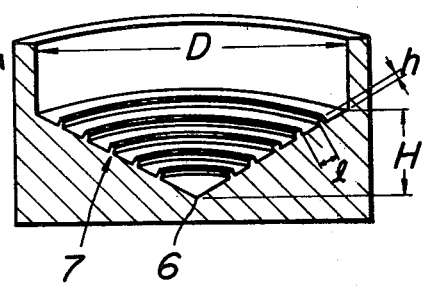
FIG. 2 is a perspective view of another embodiment of an agglutination analyzing vessel according to the invention, partly shown in section.

FIG. 2 shows another embodiment of an agglutination analyzing vessel according to the invention. In this embodiment, an agglutination analyzing vessel 5 is provided at its conically inclined base surface with a plurality of protrusions 7 leading from the lowest point 6 of an inverted conical surface along the inclined surface to the top periphery thereof located at substantially the middle point of the inner wall of the vessel and concentrically arranged about the bottom point 6 as its center in a continuous and regular manner. Each protrusion 7 has a height h of 2 to 50 $\mu$m and a distance l between adjacent protrusions 7, 7 in the inclined direction of 5 to 200 $\mu$m. An inner diameter D of the vessel 5, height H and inclined angle of the inclined base surface with respect to the horizontal base surface of the vessel are substantially the same as those shown in FIG. 1. The vessel 5 is formed of plastic material having a chemically resistant property and made integral into one body.

In the vessel 5 constructed as above described, the protrusions 7 function to prevent the particles sedimented on the inclined base surface of the vessel from slipping down therealong toward the lowest point 6 of the inclined base surface so as to form a stable substrate on the inclined base surface, thereby obtaining clear and precise agglutination patterns in the same manner as in the case of the vessel 1 shown in FIG. 1.

In the embodiments shown in FIGS. 1 and 2, the depressed portions 3 and protruded portions 7 are regularly arranged along a substantially overall inclined base surface region of the vessels 1 and 5, respectively. But, these depressed and protruded portions 3, 7 may be regularly arranged along a portion of the inclined base surface of the vessels 1 and 5, respectively, for the purpose of obtaining the same effect as those obtained by the vessels shown in FIGS. 1 and 2.

Figure 3:
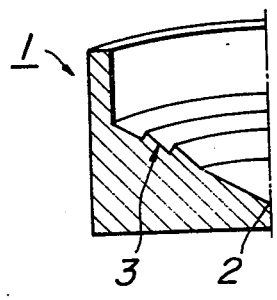
FIG. 3 is a perspective view of a further embodiment of an agglutination analyzing vessel according to the invention, partly shown in section.
Figure 4:
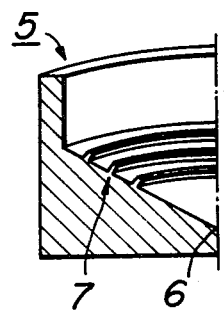
FIG. 4 is a perspective view of a still further embodiment of an agglutination analyzing vessel according to the invention, partly shown in section.

FIGS. 3 and 4 show other embodiments in which the depressed portions 3 shown in FIG. 1 and the protruded portions 7 shown in FIG. 2 are regularly arranged along a portion of the inclined base surface of the vessels 1 and 5, respectively. That is, a plurality of depressed and protruded portions 3, 7 are regularly arranged along that region of the inclined base surface of the vessels 1 and 5 which is separated from the lowest portions 2, 6 of the inclined base surface and concentrically arranged about the lowest portions 2, 6 as its center, respectively.

As stated hereinbefore, the agglutination analyzing vessel according to the invention is capable of forming a stable substrate on the inclined base surface of the vessel, and as a result, the vessel can be applied to the above mentioned blood type identifying methods with or without the immunological agglutination reaction and is capable of forming stable, clear, and precise agglutination patterns not only in the case of identifying the blood types of particles having a strong agglutinating force and of an incomplete antibody having a weak agglutinating force but also in the case of effecting analysis by means of immunological agglutination reaction. As a result, the vessel according to the invention renders it possible to easily and precisely determine the blood types by sight reading. If the vessel is formed of a transparent material, the agglutination pattern can be photoelectrically detected by light transmitted through the inclined base surface of the vessel, thereby effecting the immunological analysis in a precise manner.

Figure 5A:
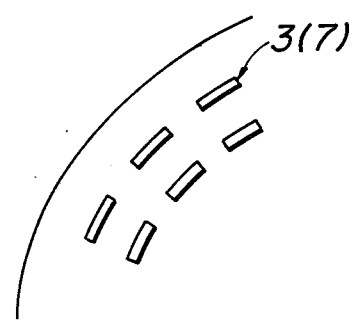
FIGS. 5A and 5B are diagrammatic views of two examples in which a plurality of depressed or protruded portions are regularly arranged.
Figure 5B:
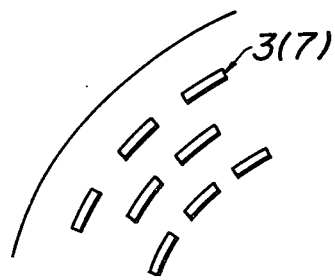

The invention is not limited to the above described embodiments, but various changes and alterations may be made. For example, the depressed portions 3 shown in FIGS. 1 and 3 are not limited to a saw-toothed shape in section. The depressed portions 3 may be made concave in section. In the above described embodiments, the depressed portions 3 shown in FIG. 1 and the protruded portions 7 shown in FIG. 2 are continuously and concentrically arranged about the lowest points 2, 6 of the conical base surface of the vessel 1, 5 as their centers. Alternatively, these depressed portions 3 and protruded portions 7 may be intermittently and concentrically arranged as shown in FIGS. 5A and 5B, respectively. In the embodiment shown in FIG. 5A, the intermittent depressed and protruded portions 3, 7 are aligned in the inclined direction. In the embodiment shown in FIG. 5B, these intermittent depressed and protruded portions 3, 7 are arranged in zigzag in the inclined direction. In FIGS. 5A and 5B, the intermittent depressed and protruded portions 3, 7 are made rectangular in shape, but they may be made circular or elliptical in shape. In addition, these depressed and protruded portions may be spirally arranged instead of concentrically arranged. Moreover, in order to prevent spattering of the test liquid, test medicine or the like when the liquid is introduced into the vessel, the inner wall of the vessel may be tapered so as to be enlarged toward the opening portion thereof. The thickness of the side surface and inclined base surface of the vessel may be made substantially uniform. If the stable substrate is formed on the inclined base surface, stable, clear and precise agglutination patterns are formed irrespective of the agglutination or non-agglutination of the particles. The inclined base surface may be formed on one portion of the base surface of the vessel. In addition, the inclined base surface may be formed on one side surface only of the vessel. In addition, the vessel may be box-shaped and the base surface thereof may be inclined at one side or at both sides so as to make the vessel V-shaped in section. On such inclined base surface there may be formed the above mentioned depressed or protruded portions. In this case, the vessel may be formed of transparent material and the light axis of the photoelectric detector may be crossed with the inclined base surface so as to detect the agglutination patterns by means of the transmitted light.

Experimental tests have demonstrated the result that it is preferable to incline the base surface at an angle on the order of 30° with respect to the horizontal surface. This inclined angle, depth and length of the depressed portions, height of the protruded portions and distance between adjacent protruded portions may suitably be changed so as to adjust the agglutination reaction time and sensitivity.

Figure 6:
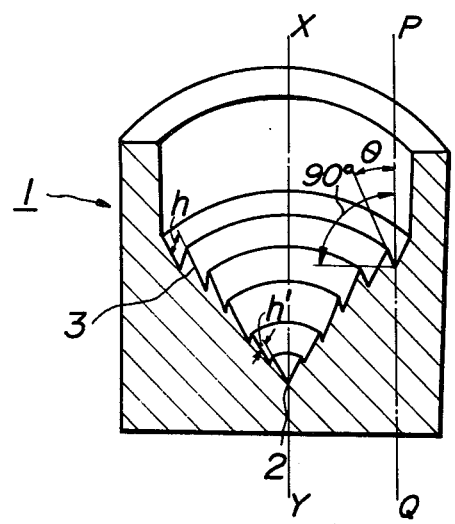
FIGS. 6 and 7 are perspective views of other embodiments of an agglutination analyzing vessel according to the invention, partly shown in section, respectively.

FIG. 6 shows another embodiment in which the sawtoothed shape of the depressed portions 3 shown in FIG. 1 is so deformed that each sawtooth is inclined at an angle $\theta$ which is smaller than 90° with respect to a line P-Q which is parallel with a center axis X-Y of the vessel 1 so as to form a sawtooth having a sharp upper edge and that the maximum depth h is gradually decreased from the top periphery of the inverted conical base surface of the vessel to the lowest point 2 where the maximum depth h' is the smallest. An angle θ which is 0° to 90° with respect to the line PQ can efficiently hold the settling down particles.

The use of such saw-toothed depressed portions 3 renders it possible to efficiently hold the settling particles. Experimental tests have shown the result that in the case of human blood the maximum depth can be changed from h=20 μm to h'=12 μm and that in the case of sheep blood the maximum depth can be changed from h=12 μm to h'=5 μm.

Figure 7:
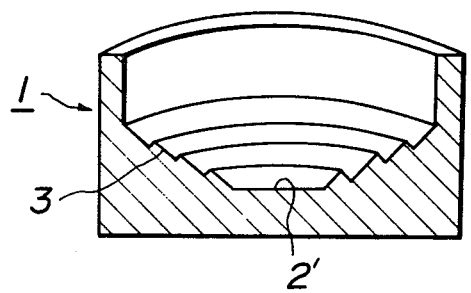

FIG. 7 shows another embodiment in which the lowest point 2 shown in FIG. 1 is deformed into a lowest flat region 2'. The use of such lowest flat region 2' ensures an excellent discrimination when the particles are agglutinated, but some particles are not agglutinated and slipped down along the substrate and collected in the lowest flat region 2' of the inclined base surface. This is due to the fact that the lowest flat region 2' makes the particles thus collected thereon distribute uniformly and the light transmission property of the pattern formed thereon uniform, thereby discriminating the difference between the particle in the agglutinated state and the particles in the non-agglutinated state.

What is claimed is:

1. In a particle agglutination analyzing vessel having a base surface wherein particles can settle down along said base surface so as to form agglutination patterns on the base surface of the vessel to thereby effect an immunological analysis, wherein the improvement comprises said base surface is provided on at least one portion thereof with an inclined surface which is provided on at least one portion thereof with a plurality of regularly arranged engravings, said engravings being of such a depth and length to permit the formation of a clear and precise agglutination pattern of said settling down particles on said inclined base surface.

2. The particle agglutination analyzing vessel according to claim 1, wherein said plurality of engravings are led from the lowest point of an inverted conically inclined base surface of the vessel along the inclined base surface to the top periphery and regularly and concentrically arranged about the lowest point as its center along a substantially overall inclined base surface region of the vessel.

3. The particle agglutination analyzing vessel according to claim 1, wherein said plurality of engravings are intermittently and concentrically arranged about the lowest point of the conically inclined base surface of the vessel as its center, said engravings being aligned in the inclined direction.

4. The particle agglutination analyzing vessel according to claim 1, wherein said plurality of engravings are intermittently and concentrically arranged about the lowest point of the conically inclined base surface of the vessel as its center, said engravings being arranged in zigzag in the inclined direction.

5. The particle agglutination analyzing vessel according to claim 1, wherein said plurality of engravings are spirally arranged.

6. The particle agglutination analyzing vessel according to claim 1, wherein said plurality of engravings are composed of a plurality of depressions each having a depth of 2 to 50 μm and a length in the inclined direction of 5 to 200 μm.

7. The particle agglutination analyzing vessel according to claim 1, wherein said plurality of engravings are formed by a plurality of protrusions each having a height of 2 to 50 μm and spaced apart from each other in the inclined direction by a distance of 5 to 200 μm.

8. The particle agglutination analyzing vessel according to claim 6, wherein said plurality of depressions are of sawteeth shaped ones, each sawtooth being inclined at an angle θ which is 0° to 90° with respect to the center axis of the vessel so as to form a sawtooth having a sharp upper edge, and the maximum depth being gradually decreased from the top periphery of the inverted conical base surface of the vessel to the lowest point where the maximum depth is the smallest.

9. The particle agglutination analyzing vessel according to claim 5, wherein said plurality of depressions are of sawteeth shaped ones, each sawtooth being inclined at an angle θ which is 0° to 90° with respect to the center axis of the vessel so as to form a sawtooth having a sharp upper edge, and the maximum depth being gradually decreased from the top periphery of the inverted conical base surface of the vessel to the lowest point where the maximum depth is the smallest.

10. The particle agglutination analyzing vessel according to claim 2, wherein said lowest point of an inverted conically inclined base surface of the vessel is deformed into a lowest flat region.

11. The particle agglutination analyzing vessel according to claim 1, wherein said plurality of engravings are composed of a plurality of grooves each of which is V-shaped in section.

* * * * *